(12) United States Patent
Purpura et al.

(10) Patent No.: US 11,026,991 B2
(45) Date of Patent: Jun. 8, 2021

(54) COMPOSITIONS AND METHODS OF USE THEREOF TO PROMOTE MUSCLE GROWTH AND FUNCTION

(71) Applicant: Worlds Greatest Ingredients, LP, Lewisville, TX (US)

(72) Inventors: Martin Purpura, Austin, TX (US); Ralf Jaeger, Milwaukee, WI (US); Shawn Wells, Frisco, TX (US); Kylin Lao, Lewisville, TX (US); Anton Fliri, Stonington, CT (US)

(73) Assignee: Ingenious Ingredients, LP, Lewisville, TX (US)

( * ) Notice: Subject to any disclaimer, the term of this patent is extended or adjusted under 35 U.S.C. 154(b) by 0 days.

(21) Appl. No.: 16/388,490

(22) Filed: Apr. 18, 2019

(65) Prior Publication Data

US 2019/0321437 A1    Oct. 24, 2019

Related U.S. Application Data

(60) Provisional application No. 62/659,474, filed on Apr. 18, 2018.

(51) Int. Cl.
  *A61K 38/05*    (2006.01)
  *A61P 21/06*    (2006.01)
  *A61K 38/06*    (2006.01)
  *A61K 31/197*   (2006.01)

(52) U.S. Cl.
  CPC .......... *A61K 38/05* (2013.01); *A61K 31/197* (2013.01); *A61K 38/06* (2013.01); *A61P 21/06* (2018.01)

(58) Field of Classification Search
  CPC ...... A61K 31/197; A61K 38/05; A61K 38/06; A61P 21/06
  See application file for complete search history.

(56) References Cited

U.S. PATENT DOCUMENTS

| 10,201,513 B2* | 2/2019 | Hamill ............... A61K 38/06 |
| 10,238,617 B2* | 3/2019 | Hamill ............... A23L 33/175 |
| 10,471,034 B2* | 11/2019 | Hamill ............... A61K 38/06 |
| 2008/0305151 A1 | 12/2008 | Sakai et al. |
| 2009/0105123 A1 | 4/2009 | Tisdale et al. |
| 2009/0124560 A1 | 5/2009 | Morifuji et al. |
| 2010/0286034 A1 | 11/2010 | Broecke Van Den et al. |
| 2015/0132440 A1 | 5/2015 | Owoc |

FOREIGN PATENT DOCUMENTS

WO    2014134225 A2    9/2014

OTHER PUBLICATIONS

Shimomura et al. Branched-Chain Amino Acid Supplementation Before Squat Exercise and Delayed-Onset Muscle Soreness. International Journal of Sport Nutrition and Exercise Metabolism, 2010, vol. 20, pp. 236-244. (Year: 2010).*

* cited by examiner

*Primary Examiner* — Marcela M Cordero Garcia

(74) *Attorney, Agent, or Firm* — Dentons Davis Brown, P.C.; Matthew Coryell

(57) ABSTRACT

The disclosed compositions and methods relate to the increasing muscle mass, preventing muscle atrophy, promoting muscle growth, as well as treatment of various other conditions and diseases. In certain aspects, the disclosed compositions are comprised dileucine and leucine and pharmaceutically acceptable salts thereof. In certain aspects, disclosed compositions are administered to subjects in need thereof to increase muscle mass, prevent muscle atrophy, and/or promote muscle growth.

20 Claims, 15 Drawing Sheets

COMPOSITIONS AND METHODS OF USE THEREOF TO PROMOTE MUSCLE GROWTH AND FUNCTION

CROSS-REFERENCE TO RELATED APPLICATION(S)

This application claims priority to U.S. Provisional Application No. 62/659,474 filed Apr. 18, 2018 and entitled "COMPOSITIONS AND METHODS OF USE THEREOF TO PROMOTE MUSCLE GROWTH," which is hereby incorporated by reference in its entirety under 35 U.S.C. § 119(e).

BACKGROUND

Increasing muscle function is a key objective from professional athletes to fitness enthusiasts. Furthermore, preserving muscle function is critical to healthy aging. The disclosure relates to compositions and methods of using such compositions for increasing muscle mass of a subject or for preventing muscle atrophy of a subject. The disclosure further relates to compositions and methods of using such compositions for enhancing the protein concentration or muscle mass of a mammal and a method for enhancing the protein concentration or muscle mass in a mammal. Furthermore, the disclosure relates to compositions and methods of using such compositions for increasing muscle mass of a subject or for preventing muscle atrophy of a subject. The muscle atrophy-preventing composition is remarkably effective in preventing muscle mass decline and increasing muscle mass, and thus is useful in preventing and treating various muscle diseases, such as sarcopenia and disuse muscle atrophy.

BRIEF SUMMARY

Described herein are compositions for increasing muscle mass, muscle function, and/or preventing muscle atrophy. In certain aspects, the compositions comprise dileucine, leucine, and a pharmaceutically acceptable carrier thereof. In further aspects, the dileucine is present from about 10% to 90% (w/w). In further aspects, the dileucine is present from about 20% to 80% (w/w). In further aspects, wherein the dileucine is present from about 30% to 70% (w/w). In further aspects, the dileucine is present from about 40% to 60% (w/w). In still further aspects, the dileucine is present from about 50% (w/w).

Described herein are various embodiments relating to compositions of and methods for increasing muscle mass or strength devices and/decreasing or treating muscle atrophy. In certain aspects, disclosed is a method for increasing muscle mass and/or muscular strength in a subject, by administering to the subject an effective amount of a composition that comprises at least one amino acid or peptide chosen from: di-leucine, tri-leucine, and Leu-Leu-R, wherein R is an amino acid or an amino acid derivative, and pharmaceutically acceptable salts thereof. In certain aspects, the compound is di-leucine. In certain aspects, the at least one amino acid or peptide comprises leucine and di-leucine. In further aspects the dileucine is present from about 10% to about 90% (w/w). In further aspects, the dileucine is present from about 30% to about 70% (w/w). In still further aspects, the dileucine is present at about 50% (w/w).

In further aspects, the composition of a salt of di-leucine acetate. In certain aspects, the composition is Leu-Leu-R and R is a branched-chain amino acid. In further aspects, R is an essential amino acid. In yet further aspects, R is a conditionally essential amino selected from the group consisting of: arginine, cysteine, glutamine, glycine, proline, and tyrosine. In exemplary embodiments, R is tyrosine. According to certain alternative embodiments, R is a non-essential amino selected from the group consisting of: alanine, aspartic acid, asparagine, glutamic acid, serine, selenocysteine and pyrrolysine. In further alternative embodiments, R is an amino acid derivative selected from a list consisting of: creatine, carnitine, creatinol, beta-alanine, taurine, and beta-hydroxy beta-methylbutyrate.

In various embodiments the administration of the composition to the subject synergistically increases the plasma levels of leucine relative to administration of a composition comprising leucine without dileucine. In certain aspects, the administration of the composition to the subject synergistically increases muscle mass and/or muscular strength relative to administration of a composition comprising leucine without dileucine.

Further disclosed herein is a method for preventing or treating muscle atrophy in a subject comprising administering to the subject an effective amount of a composition that comprises at least one amino acid or peptide chosen from: di-leucine, tri-leucine, and Leu-Leu-R, wherein R is an amino acid or an amino acid derivative. In certain aspects the compositions comprises leucine and dileucine. In certain aspects, the method is used to treat or prevent muscle atrophy that is the result of sarcopenia. In further aspects, the muscle atrophy is the result of cachexia. In still further aspects, the muscle atrophy is the result muscle immobilization.

In some aspects the dileucine is present from about 10% to 90% (w/w). In further aspects, the dileucine is present from about 30% to 70% (w/w). In further aspects, the dileucine is present at about 50% (w/w).

In various aspects, the administration of the composition to the subject synergistically increases the plasma levels of leucine relative to administration of a composition comprising leucine without dileucine. In certain aspects the composition is administered in a therapeutically effective amount.

Further disclosed herein is a method improving cognition or preventing age-related loss of memory/cognition in a subject, the method comprising administering to the subject a therapeutically or prophylactically effective amount of a composition comprising a compound selected from a list comprising: di-leucine, tri-leucine, and Leu-Leu-R, wherein R is an amino acid or an amino acid derivative. In certain aspects, administration of the composition enhances BDNF levels. In further aspects, administration of the composition enhances NGF. In yet further aspects, the composition is administered in a neuroprotective amount.

Further disclosed herein are compositions for the treatment of conditions comprising dileucine, leucine, and pharmaceutically acceptable carriers thereof. In certain aspects the condition is at least one of obesity, immune system function associated disorders, insulin secretion associated disorders, diabetes, virulence associated conditions, cardiovascular disorder, cardiac disorders, degenerative diseases, sarcopenia, ocular disease, fibrotic diseases, aging associated disorders, improving skin hydration and collagen synthesis, liver disease, Crohn's disease.

While multiple embodiments are disclosed, still other embodiments of the disclosure will become apparent to those skilled in the art from the following detailed description, which shows and describes illustrative embodiments of the disclosed apparatus, systems and methods. As will be realized, the disclosed apparatus, systems and methods are capable of modifications in various obvious aspects, all without departing from the spirit and scope of the disclosure. Accordingly, the drawings and detailed description are to be regarded as illustrative in nature and not restrictive.

DETAILED DESCRIPTION

Figure 1:
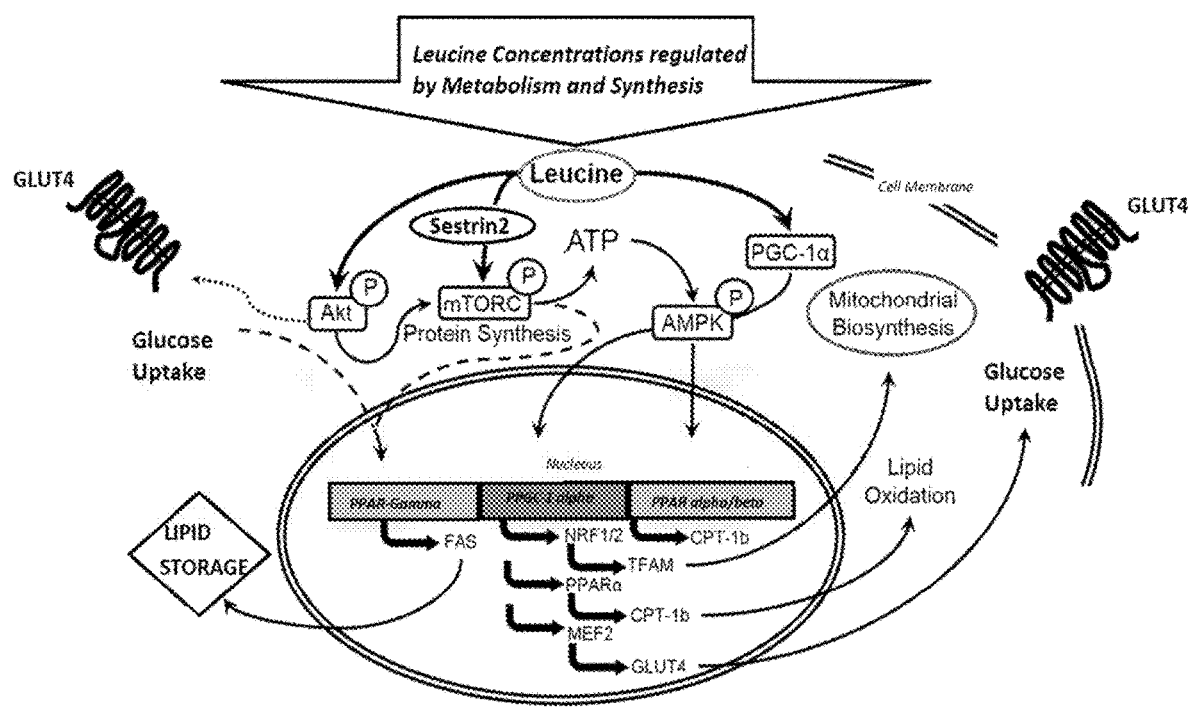
FIG. 1 is a schematic representation of the leucine processing pathways, according to certain embodiments.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

As used herein, the term "subject" refers to the target of administration, e.g. a subject. Thus the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more muscle disorders prior to the administering step. In some aspects of the disclosed method, the subject has been diagnosed with a need for increasing muscle mass prior to the administering step. In some aspects of the disclosed method, the subject has been diagnosed with a need for increasing muscle mass prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a muscle atrophy disorder" means having been subjected to a physical examination by a person of skill, for example, a physician, and found to have a condition that can be diagnosed or treated by a compound or composition that can increase muscle mass. As a further example, "diagnosed with a need for increasing muscle mass" refers to having been subjected to a physical examination by a person of skill, for example, a physician, and found to have a condition characterized by muscle atrophy or other disease wherein increasing muscle mass would be beneficial to the subject. Such a diagnosis can be in reference to a disorder, such as muscle atrophy, and the like, as discussed herein.

As used herein, the phrase "identified to be in need of treatment for a disorder," or the like, refers to selection of a subject based upon need for treatment of the disorder. For example, a subject can be identified as having a need for treatment of a disorder (e.g., a disorder related to muscle atrophy) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

Without wishing to be bound to any particular theory of mechanism of action, the levels of leucine within an organism is indicative of the organisms physiological state, including how much food is available, how much insulin is going to be needed, and whether new muscle mass can be made. For example, leucine decreases protein degradation in humans suggesting that leucine is a regulator of protein metabolism in humans. Furthermore leucine stimulates Akt and protein synthesis resulting in increased ATP demands. These increases in energy demands stimulate activities and cellular expression levels of metabolic regulators including AMPK, PPARβ/δ, and PGC-1α leading to concomitant increases in oxidative metabolism, mitochondrial biogenesis, and GLUT4 content. Elevated GLUT4 contents in turn promote increased glucose uptake to support rising energy needs. Augmented energy uptake promotes simultaneous substrate oxidation and storage (in-part through increased PPARγ) leading to increased cellular lipid content.

As seen in FIG. 1, Sestrin2 is central to leucin mediated energy sensing and metabolism regulating processes. Sestrin 2 connects cellular and systemic concentrations of leucine to the control of organismal metabolism and growth. Thus, when leucine binds to Sestrin2, it releases Sestrin2 from a complex with the mTORC1 regulatory factor GATOR2, which, upon release, activates the mTORC1 complex. Thus, it is well recognized that modulating the activity of this leucine and mTORC mediated process may offer new strategies for treatment of a broad range of conditions and diseases.

The compositions disclosed herein are capable of affecting leucine concentrations in organisms, and thereby affecting mTORC activity are anticipated to have a broad range of therapeutic utilities. In various embodiments disclosed herein are compositions consisting of combinations of leucine and dipeptide dileucine that may substantially alter the regulation of leucine concentrations in vivo and have a broad range of therapeutic benefits. In various aspects the benefits of the herein described compounds may include the ability to increase muscle growth. In various other aspects the disclosed compositions may be used for supporting muscle homeostasis, preventing and/or treating sarcopenia, and affecting satiety.

Disclosed herein are compositions and methods for promoting muscle growth and/or preventing or treating muscle atrophy. In certain aspects, the disclosed method comprises administering a composition to a subject where the composition comprises the compound di-leucine. Di-leucine refers to a dipeptide comprised of two L-leucines. In certain aspects, di-leucine can have the structure:

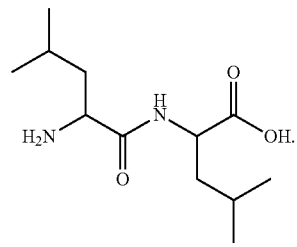 [SMILES: CC(C)CC(N)C(=O)NC(CC(C)C)C(=O)O]

Di-leucine may also be referred to as L-Leucyl-L-leucine or Leu-Leu and has number CAS #3303-31-9.

In certain aspects, disclosed are compositions for increasing muscle mass comprising dileucine, leucine, and a pharmaceutically acceptable carrier thereof. In various aspects dileucine is present from about 10% to 90% (w/w). In further aspects, the dileucine is present from about 20% to 80% (w/w). In further aspects, wherein dileucine is present from about 30% to 70% (w/w). In further aspects, dileucine is present from about 40% to 60% (w/w). In still further aspects, dileucine is present from about 50% (w/w).

In alternative embodiments, dileucine is present from about 10%-90% (w/w) and leucine is present from about 90%-10% (w/w). In further embodiments, dileucine is present from about 20%-80% (w/w) and leucine is present from about 80%-20% (w/w). In further embodiments, dileucine is present from about 30%-70% (w/w) and leucine is present from about 70%-30% (w/w). In further embodiments, dileucine is present from about 40%-60% (w/w) and leucine is present from about 60%-40% (w/w). In further embodiments, dileucine is present at about 50% (w/w) and leucine is present at about 50% (w/w).

In certain aspects, the disclosed method comprises administering a composition comprising di-leucine salt. In exemplary embodiments, the composition is a di-leucine acetate salt, which may have the structure:

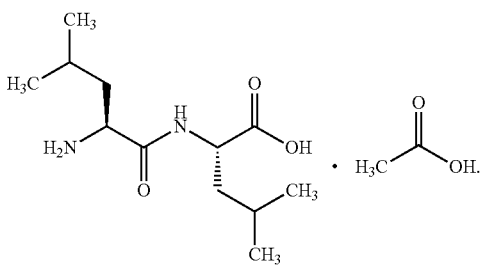

In certain aspects, the disclosed method comprises administering a composition to a subject where the composition comprises tri-leucine. Trileucine means a tripeptide comprising of three L-leucines. In certain aspects, tri-leucine has the structure:

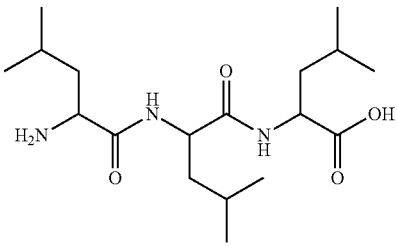 [SMILES: CC(C)CC(N)C(=O)NC(CC(C)C)C(=O)NC(CC(C)C)C(=O)O]

Tri-leucine may also be referred to as TRILEUCINE; LEU-LEU-LEU; H-LEU-LEU-LEU-OH; L-LEUCYL-LEUCYLLEUCINE; leucyl-leucyl-leucine; Leu-leu-leu-crystalline; L-LEUCY-L-LEUCYL-L-LEUCINE; L-LEUCYL-L-LEUCYL-L-LEUCINE; Leu-Leu-Leu-OH≥S)-2-((S)-2-((S)-2-Amino-4-methylpentanamido)-4-methylpentanamido)-4-methylpentanoic acid.

In further aspects, the disclosed method comprises administering a composition to a subject where the composition comprises tripeptide comprising two L-Leucine units and one amino acid or amino acid derivative. According to certain embodiments, the amino acid is selected from a group of branched-chain amino acids (BCAA), including, but not limited to, isoleucine, leucine, and valine. In further embodiments, the amino acid is selected from the group of essential amino acids, including, but not limited to, histidine, isoleucine, leucine, lysine, methionine, phenylalanine, threonine, tryptophan, and valine. In still further embodiments, the amino acid is selected from the group of conditionally essential amino acids including, but not limited to, arginine, cysteine, glutamine, glycine, proline, and tyrosine. According the certain embodiments, the conditionally essential amino acid is tyrosine. In exemplary embodiments, the composition comprises a di-leucine tyrosine that has the structure:

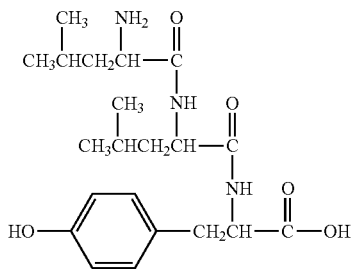

In still further embodiments, the amino acid is selected from the group of non-essential amino acids including, but not limited to, alanine, aspartic acid, asparagine, glutamic acid, serine, selenocysteine and pyrrolsine. In yet further embodiments, the amino acid derivative is selected from the group of creatine, carnitine, creatinol, beta-alanine, taurine, and beta-hydroxy beta-methylbutyrate.

In certain aspects, disclosed is a method for increasing muscle mass and/or muscular strength in a subject comprising administering to the subject an effective amount of a composition that comprises at least one amino acid or peptide chosen from: di-leucine, tri-leucine, and Leu-Leu-R, wherein R— is an amino acid or an amino acid derivative, and pharmaceutically acceptable salts thereof. In various aspects the at least one amino acid or peptide comprises leucine and di-leucine and/or and pharmaceutically acceptable salts thereof.

In certain embodiments, dileucine is present from about 10% (w/w) to about 90% (w/w). In further embodiments, dileucine is present from about 30% to 70% (w/w). In further embodiments, dileucine is present at about 50% (w/w).

In various alternative embodiments, dileucine is present from about 10%-90% (w/w) and leucine is present from about 90%-10% (w/w). In further embodiments, dileucine is present from about 30%-70% (w/w) and leucine is present from about 70%-30% (w/w). In further embodiments, dileucine is present at about 50% (w/w) and leucine is present at about 50% (w/w).

In these and other embodiments, the administration of the composition to the subject synergistically increases the plasma levels of leucine relative to administration of a composition comprising leucine without dileucine. Additionally, the administration of the composition to the subject synergistically increases muscle mass and/or muscular strength relative to administration of a composition comprising leucine without dileucine.

In various aspects the compositions comprises at least about 95% dileucine; and between about 0.1%-5% tri-leucine, and pharmaceutically acceptable salts thereof. In further aspects, the tri-leucine is present at an amount between about 0.1%-3% and the composition further comprising about 0.1%-2% tetra-leucine. In yet further aspects, the tri-leucine is present at an amount of about 0.4% and the tetra-leucine is present at an amount of about 0.2%.

According to certain alternative embodiments, the composition comprises at least about 95% dileucine; and between about 0.1%-5% tetra-leucine, and pharmaceutically acceptable salts thereof.

In certain aspects of the foregoing embodiments, the composition is substantially free of leucine.

According to certain further aspects, disclosed is a method for increasing muscle mass and/or muscular strength in a subject, the method comprising administering to the subject an effective amount of a composition comprising at least about 95% dileucine; and between about 0.1%-5% leucine, and pharmaceutically acceptable salts thereof. According to exemplary aspects of these embodiments, In certain aspects, the compositions administered according to the disclosed methods are produced through bacterial fermentation. According to these embodiments, fermentation techniques are employed utilizing di-/tri-/tetra-peptide-forming enzymes that directly links amino acids, followed by extraction processes.

In certain aspects, disclosed herein are methods to promote muscle growth through the administration of an effective amount of one or more compositions disclosed herein.

According to certain aspects, administration of effective amounts of the disclosed compositions results in higher levels of blood plasma leucine through improved delivery and/or transport. In certain further aspects, administration of effective amounts of the disclosed compositions results in greater level of muscle protein synthesis per gram in the subject. In yet further aspects, administration of effective amounts of the disclosed compositions results in faster transport to plasma and faster and optimal MPS (muscle protein synthesis) in the subject. In still further aspects, administration of effective amounts of the disclosed compositions results in improved muscle accretion in the subject.

According to certain embodiments, compositions disclosed herein may be administered in conjunction with a strength training regime. As will be appreciated by a person having skill in the art, administration of effective amounts of the disclosed compositions results in improved strength and improved athletic performance/ergogenesis in the subject.

In one aspect, the disclosed compounds inhibit muscle atrophy. In a further aspect, the disclosed compounds increase muscle mass. In a still further aspect, the disclosed compounds induce muscle hypertrophy. In a yet further aspect, the disclosed compounds inhibit of muscle atrophy and increase muscle mass. In an even further aspect, the disclosed compounds inhibit of muscle atrophy and induce muscle hypertrophy. In a further aspect, the inhibition of muscle atrophy is in a subject. In an even further aspect, the increase in muscle mass is in a subject. In a still further aspect, the subject is a mammal. In a yet further aspect, the mammal is a human.

In certain aspects, administration of the disclosed compositions is effective at preventing or treating age-related muscle atrophy or sarcopenia. In further aspects, administration of the disclosed compositions is effective at preventing or treating muscle atrophy associated with muscle immobilization, such as that which frequently occurs with casting of fractured bones. In further aspects, administration of the disclosed compositions is effective at preventing or treating muscle atrophy associated with disease, such as cancer, also known as cachexia.

Disclosed herein is a method for prevention or treating muscle atrophy in a subject, the method comprises administering to the subject an effective amount of a disclosed composition. In certain aspects the composition comprises leucine and dileucine.

In various embodiments, dileucine is present from about 10% (w/w) to about 90% (w/w). In further embodiments, dileucine is present from about 30% to 70% (w/w). In further embodiments, dileucine is present at about 50% (w/w).

In various alternative embodiments, dileucine is present from about 10%-90% (w/w) and leucine is present from about 90%-10% (w/w). In further embodiments, dileucine is present from about 30%-70% (w/w) and leucine is present from about 70%-30% (w/w). In further embodiments, dileucine is present at about 50% (w/w) and leucine is present at about 50% (w/w).

According to certain aspects the composition is administered to a subject that has sarcopenia. In various aspects, the composition is administered in a therapeutically effective amount. In further aspects, the composition is administered at prophylactically effective amount, (e.g. to a subject at risk for developing sarcopenia, cachexia, or immobilization induced atrophy).

According to certain embodiments, administration of the disclosed compositions is effective at improving cognition and/or preventing or treating age-related memory loss or cognitive decline. In certain aspects, administration of the disclosed compositions increases enhances levels of brain-derived neurotrophic factor (BDNF), nerve growth factor (NGF), or is otherwise neuroprotective.

In a further aspect, the disclosed compounds increase muscle mass when administered at an oral dose of greater than about 200 mg per day in a human. In a yet further aspect, the disclosed compounds increase muscle mass when administered at an oral dose of greater than about 300 mg per day in a human. In a still further aspect, the disclosed compounds increase muscle mass when administered at an oral dose of greater than about 400 mg per day in a human. In an even further aspect, the disclosed compounds increase muscle mass when administered at an oral dose of greater than about 500 mg per day in a human. In a further aspect, the disclosed compounds increase muscle mass when administered at an oral dose of greater than about 750 mg per day in a human. In a yet further aspect, the disclosed compounds increase muscle mass when administered at an oral dose of greater than about 1000 mg per day in a human. In a still further aspect, the disclosed compounds increase muscle mass when administered at an oral dose of greater than about 2000 mg per day in a human. In an even further aspect, the disclosed compounds increase muscle mass when administered at an oral dose of greater than about 3000 mg per day in a human. In an yet further aspect, the disclosed compounds increase muscle mass when administered at an oral dose of greater than about 5000 mg per day in a human.

EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

The case study was done on a healthy 24-year-old subject weighing 180 pounds. The subject came into the laboratory fasted prior to the testing days. The subject is a resistance-trained individual that weight trains 4 days per week. On Day 1, he was randomized to consume 1 of the 2 conditions. Following, consumption of the fluid mixture (8 oz. water), plasma amino acids were measured at 30, 60, 90, and 120 minutes. A 72-hour washout took place followed by the 2nd condition following the same procedures.

The dosage used in this study was either 2 grams of di-leucine (condition Ce) or 2 grams of leucine (condition C4).

Leucine

TABLE 1

Plasma Leucine Concentrations After Ingestion of C4 and CE Conditions (nmol/l).

|    | Pre    | 30 mPost      | 60 mPost     | 90 mPost     | 120 mPost    |
|----|--------|---------------|--------------|--------------|--------------|
| C4 | 92.25  | 198.33        | 146.70       | 181.67       | 158.84       |
| Ce | 153.96 | 392.03        | 246.77       | 188.43       | 197.72       |

Percent and Delta Change Relative to Baseline Values

|    | Pre    | 30 mPost        | 60 mPost      | 90 mPost      | 120 mPost     |
|----|--------|-----------------|---------------|---------------|---------------|
| C4 | 92.25  | 115.0%, 106.09  | 59.0%, 54.45  | 96.9%, 89.42  | 72.2%, 66.59  |
| Ce | 153.96 | 154.6%, 238.07  | 60.3%, 92.81  | 22.4%, 34.47  | 28.4%, 43.76  |

Figure 2:
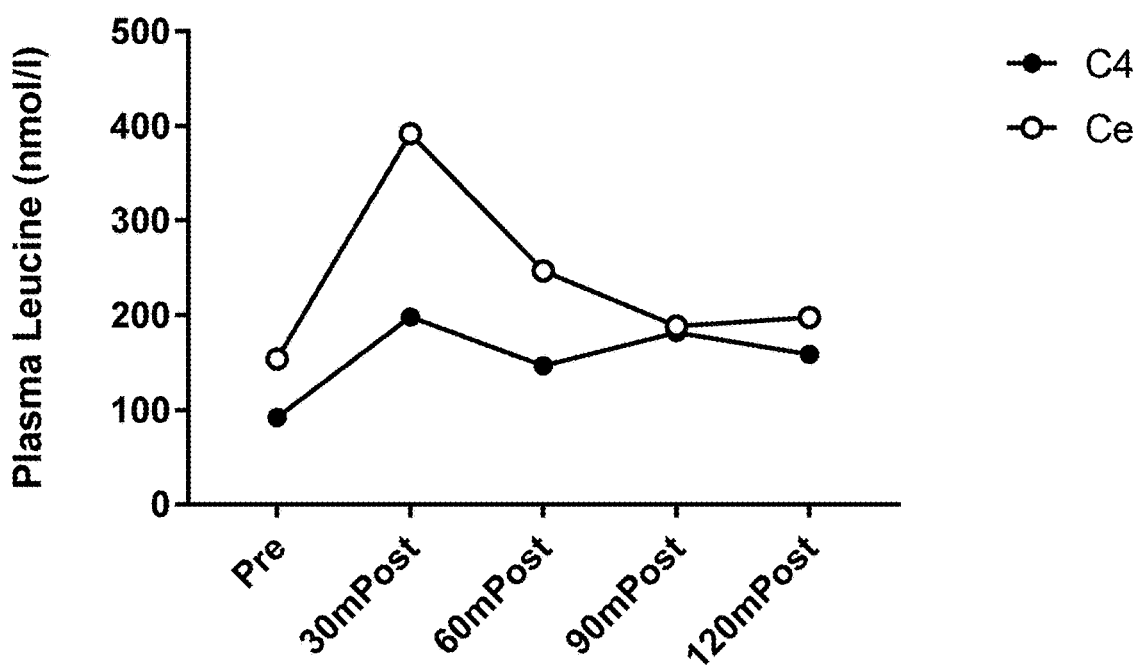
FIG. 2 shows plasma leucine concentrations following administration of disclosed compositions, according to certain embodiments.

Results: As shown in FIG. 2, both conditions demonstrated increases from baseline levels at every investigated time point. The relative increase from Pre to 30 mPost was 2.2× greater in Condition Ce over C4 (238.07 vs 106.09 nmol/ml). From Pre to 60 mPost, the relative increase was 1.7× greater in Condition Ce over C4 (92.81 vs 54.45 nmol/ml). Condition C4 demonstrated greater increases in plasma leucine concentration than Condition Ce at 90 mPost and 120 mPost relative to baseline levels; the elevation was 2.6× and 1.5× greater, respectively. The highest leucine concentration was observed in Condition Ce at 30 mPost (392.03 nmol/l) and this was the largest relative increase from Pre levels (238.07 nmol/l).

Isoleucine

TABLE 2

Plasma Isoleucine Concentrations After Ingestion of C4 and CE Conditions (nmol/l).

|    | Pre   | 30 mPost       | 60 mPost       | 90 mPost       | 120 mPost      |
|----|-------|----------------|----------------|----------------|----------------|
| C4 | 45.75 | 34.44          | 33.30          | 40.37          | 36.47          |
| Ce | 70.84 | 59.53          | 56.63          | 44.17          | 46.47          |

Percent and Delta Change Relative to Baseline Values

|    | Pre   | 30 mPost        | 60 mPost        | 90 mPost        | 120 mPost       |
|----|-------|-----------------|-----------------|-----------------|-----------------|
| C4 | 45.75 | −24.7%, −11.31  | −27.2%, −12.45  | −11.8%, −5.38   | −20.3%, −9.29   |
| Ce | 70.84 | −16.0%, −11.31  | −20.1%, −14.21  | −37.7%, −26.67  | −34.4%, −24.37  |

Figure 3:
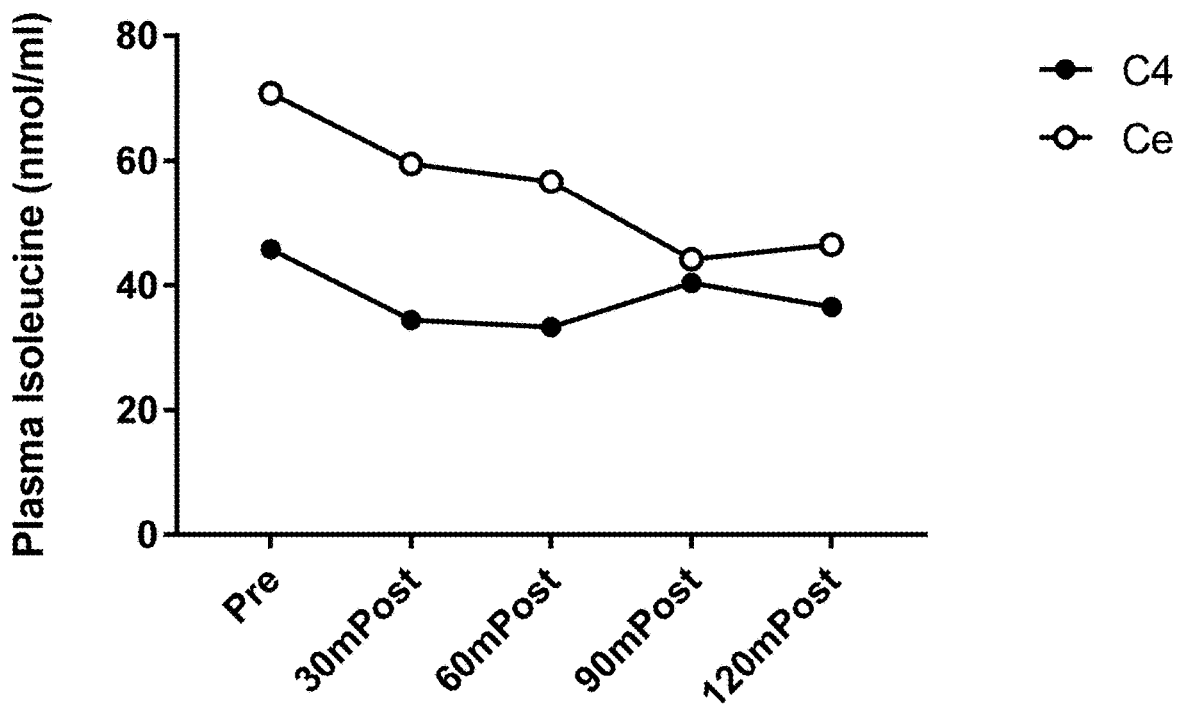
FIG. 3 shows plasma isoleucine concentrations following administration of disclosed compositions, according to certain embodiments.

Results: As shown in FIG. 3, both conditions demonstrated lower plasma isoleucine levels at 30, 60, 90, and 120 mPost ingestion (−37.7% to −11.8%).

Valine

TABLE 3

Plasma Valine Concentrations After Ingestion of C4 and CE Conditions (nmol/l).

|    | Pre    | 30 mPost      | 60 mPost       | 90 mPost       | 120 mPost      |
|----|--------|---------------|----------------|----------------|----------------|
| C4 | 230.43 | 210.39        | 200.61         | 225.20         | 234.78         |
| Ce | 373.39 | 360.08        | 320.76         | 293.97         | 287.86         |

Percent and Delta Change Relative to Baseline Values

|    | Pre    | 30 mPost       | 60 mPost        | 90 mPost        | 120 mPost       |
|----|--------|----------------|-----------------|-----------------|-----------------|
| C4 | 230.43 | −8.7%, −20.04  | −12.9%, −29.82  | −2.3%, −5.23    | 1.9%, 4.35      |
| Ce | 373.39 | −3.6%, −13.31  | −14.1%, −52.63  | −21.3%, −79.42  | −22.9%, −85.53  |

Figure 4:
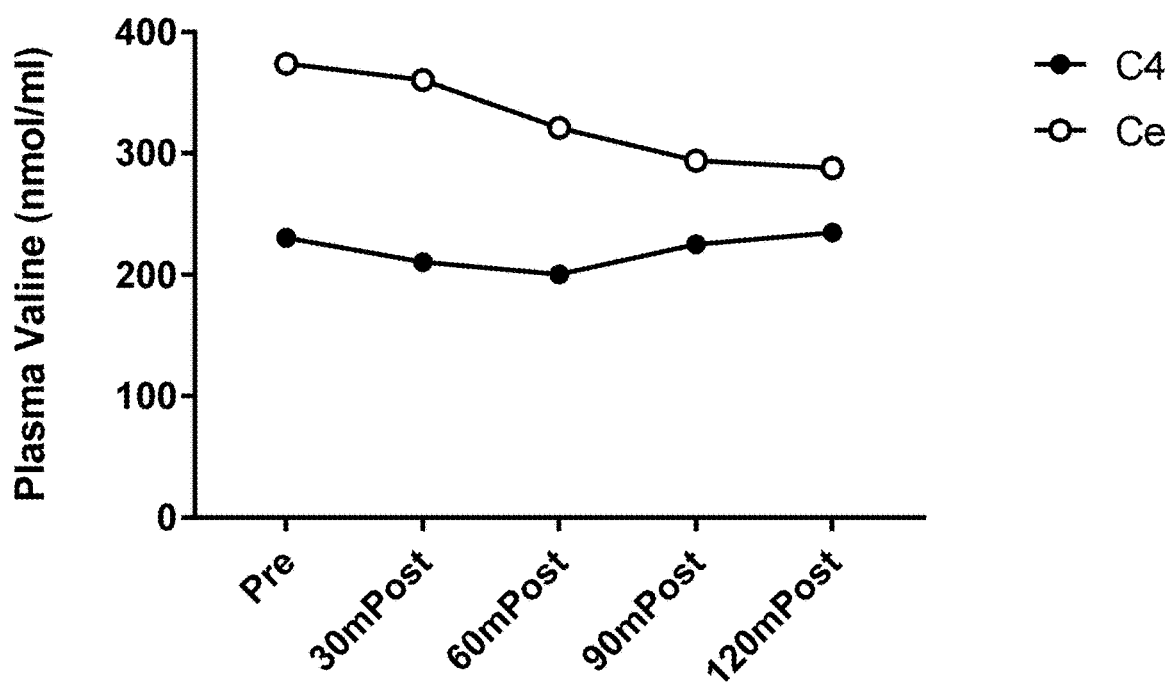
FIG. 4 shows plasma valine concentrations following administration of disclosed compositions, according to certain embodiments.

Results: As shown in FIG. 4, both conditions demonstrated decreases in plasma valine concentration over the time course (−21.3% to −2.3%). At 120 mPost, Condition C4 marginally increased over Pre values (1.9%, 4.35 nmol/l).

Total BCAAs

TABLE 4

Total Plasma BCAA Concentrations After Ingestion of C4 and CE Conditions (nmol/l).

|    | Pre | 30 mPost | 60 mPost | 90 mPost | 120 mPost |
|----|-----|----------|----------|----------|-----------|
| C4 | 368.43 | 443.16 | 380.61 | 447.24 | 430.08 |
| Ce | 598.19 | 811.64 | 624.16 | 526.56 | 532.05 |
| Percent and Delta Change Relative to Baseline Values | | | | | |
| C4 | 368.43 | 20.3%, 74.73 | 3.3%, 12.18 | 21.4%, 78.81 | 16.7%, 61.66 |
| Ce | 598.19 | 35.7%, 213.45 | 4.3%, 25.97 | −12.0%, −71.62 | −11.1%, −66.14 |

Figure 5:
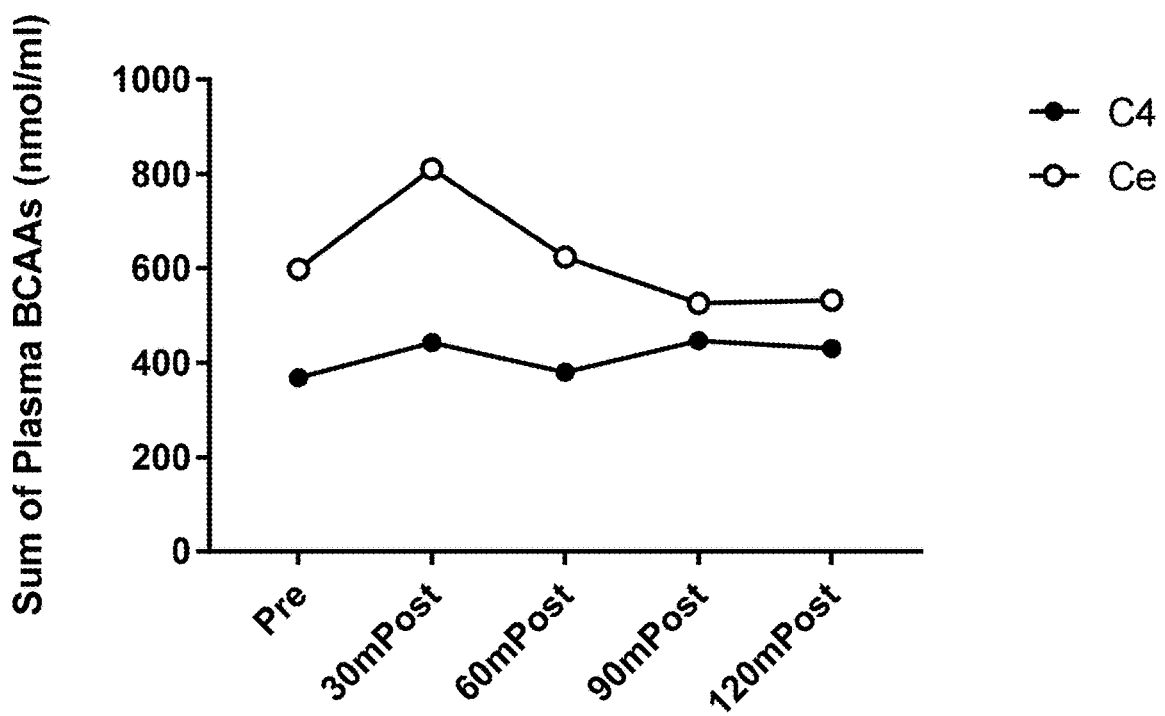
FIG. 5 shows total plasma BCAA concentrations following administration of disclosed compositions, according to certain embodiments.

Results: FIG. 5 shows total plasma BCAA concentrations after ingestion of C4 and Ce conditions. Both conditions demonstrated higher total plasma BCAA concentrations at 30 and 60 mPost ingestion. The highest elevation in plasma BCAAs was observed in Condition Ce at 30 mPost (35.7%, 213.45 nmol/l); this increase was 2.9× greater than that of Condition C4. The aforementioned result mirrors the observed response in plasma leucine concentration. Only Condition C4 maintained higher plasma BCAA concentration relative to Pre levels at 90 and 120 mPost.

Threonine

TABLE 5

Plasma Threonine Concentrations After Ingestion of C4 and CE Conditions (nmol/l).

|    | Pre | 30 mPost | 60 mPost | 90 mPost | 120 mPost |
|----|-----|----------|----------|----------|-----------|
| C4 | 87.38 | 76.42 | 75.83 | 91.05 | 90.94 |
| Ce | 107.52 | 114.61 | 113.63 | 104.12 | 105.44 |
| Percent and Delta Change Relative to Baseline Values | | | | | |
| C4 | 87.38 | −12.5%, −10.96 | −13.2%, −11.55 | 4.2%, 3.67 | 4.1%, 3.56 |
| Ce | 107.52 | 6.6%, 7.09 | 5.7%, 6.11 | −3.2%, −3.4 | −1.9%, −2.07 |

Figure 6:
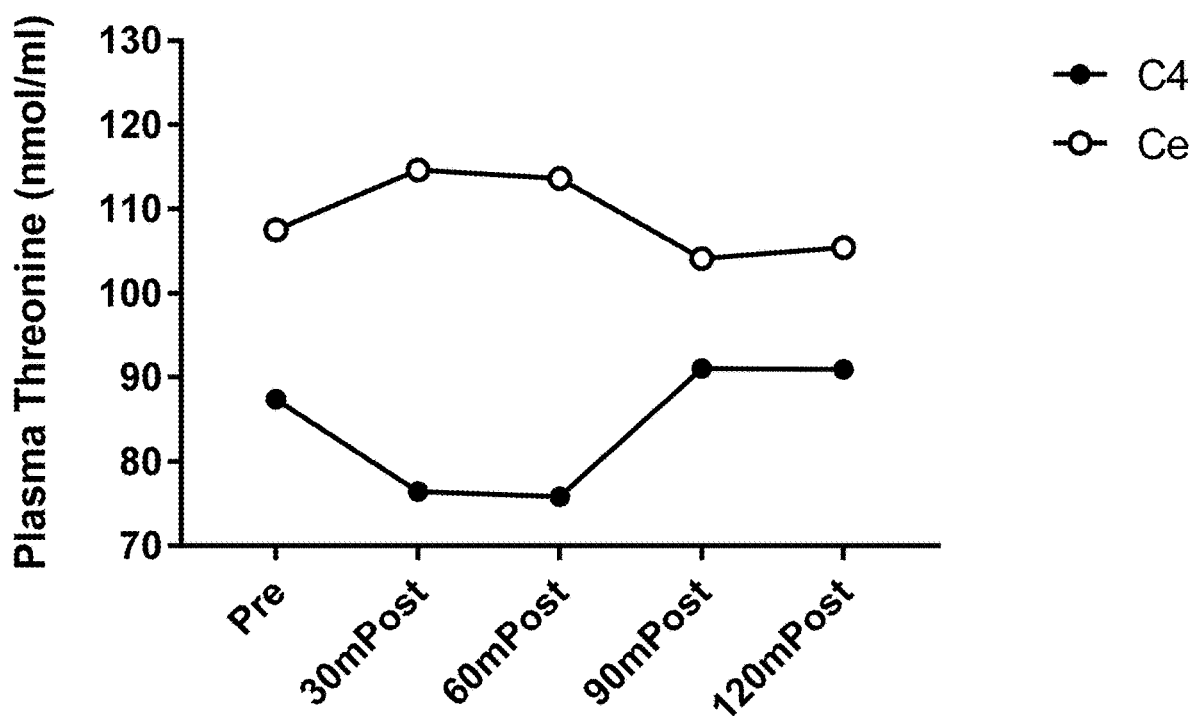
FIG. 6 shows plasma threonine concentrations following administration of disclosed compositions, according to certain embodiments.

Results: FIG. 6 shows plasma threonine concentrations after ingestion of C4 and CE conditions. An inverse response was observed between conditions regarding plasma threonine concentrations. Condition Ce demonstrated an increase in plasma threonine concentrations from Pre to 30 m and 60 m post ingestion (+6.6%, and +5.7%, respectively) while Condition C4 had decreased levels (−12.5% and −13.2%). At 90 and 120 mPost ingestion, Condition C4 had higher plasma threonine levels relative to Pre values (4.2% and 4.1%, respectively) whereas Condition Ce had lower levels (−3.2% and −1.9%).

Methionine

TABLE 6

Plasma Methionine Concentrations After Ingestion of C4 and CE Conditions (nmol/l).

|    | Pre | 30 mPost | 60 mPost | 90 mPost | 120 mPost |
|----|-----|----------|----------|----------|-----------|
| C4 | 18.77 | 16.61 | 15.94 | 19.30 | 19.19 |
| Ce | 23.07 | 25.40 | 24.09 | 21.34 | 21.39 |
| Percent and Delta Change Relative to Baseline Values | | | | | |
| C4 | 18.77 | −11.5%, −2.16 | −15.1%, −2.83 | 2.8%, 0.53 | 2.3%, 0.42 |
| Ce | 23.07 | 10.1%, 2.32 | 4.4%, 1.01 | −7.5%, −1.73 | −7.3%, −1.68 |

Figure 7:
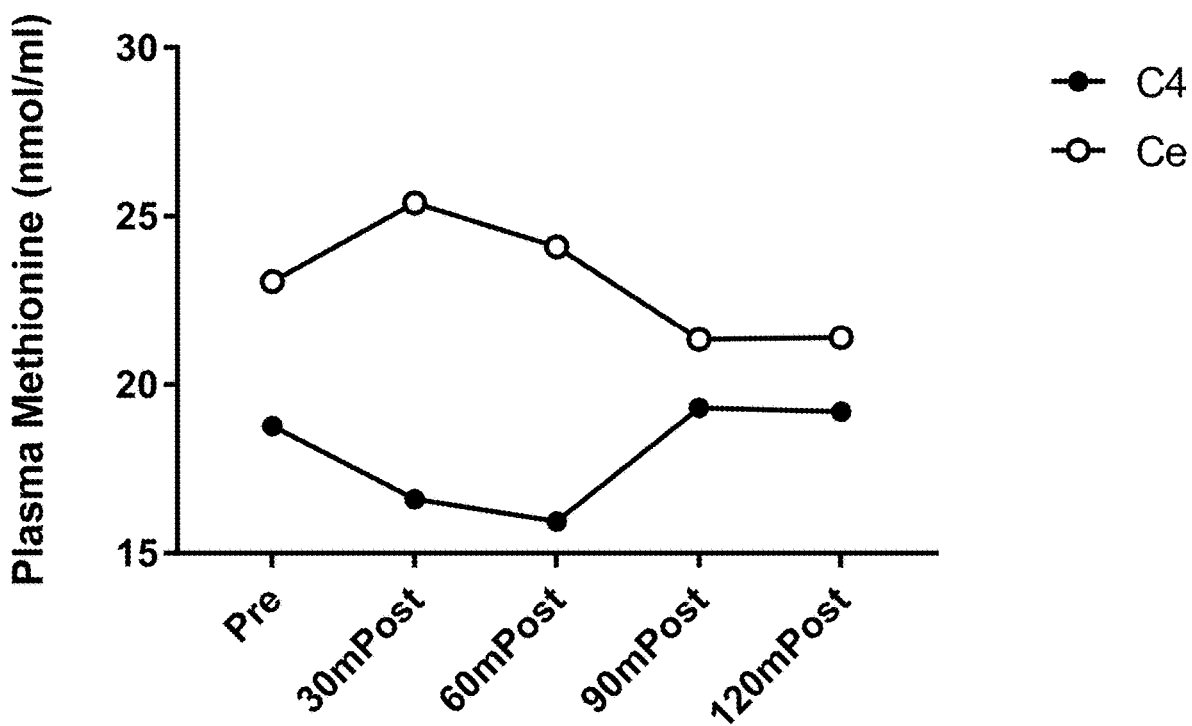
FIG. 7 shows plasma methionine concentrations following administration of disclosed compositions, according to certain embodiments.

Results: FIG. 7 shows plasma methionine concentrations after ingestion of C4 and CE conditions. An inverse response was observed between conditions regarding plasma threonine concentrations. Condition Ce demonstrated an increase in plasma threonine concentrations from Pre to 30 m and 60 m post ingestion (10.1%, and 4.4%, respectively) while Condition C4 had decreased levels (−11.5% and −15.1%). At 90 and 120 mPost ingestion, Condition C4 had higher plasma threonine levels relative to Pre values (2.8% and 2.3%, respectively) whereas Condition Ce had lower levels (−7.5% and −7.3%).

Tryptophan

TABLE 7

Plasma Tryptophan Concentrations After Ingestion of C4 and CE Conditions (nmol/l).

|    | Pre   | 30 mPost      | 60 mPost      | 90 mPost       | 120 mPost       |
|----|-------|---------------|---------------|----------------|-----------------|
| C4 | 45.00 | 40.12         | 43.54         | 46.58          | 44.81           |
| Ce | 64.51 | 63.69         | 59.42         | 57.91          | 51.29           |
|    |       | Percent and Delta Change Relative to Baseline Values | | | |
| C4 | 45.00 | −10.8%, −4.87 | −3.2%, −1.46  | 3.5%, 1.58     | −0.4%, −0.18    |
| Ce | 64.51 | −1.3%, −0.83  | −7.9%, −5.10  | −10.2%, −6.60  | −20.5%, −13.23  |

Figure 8:
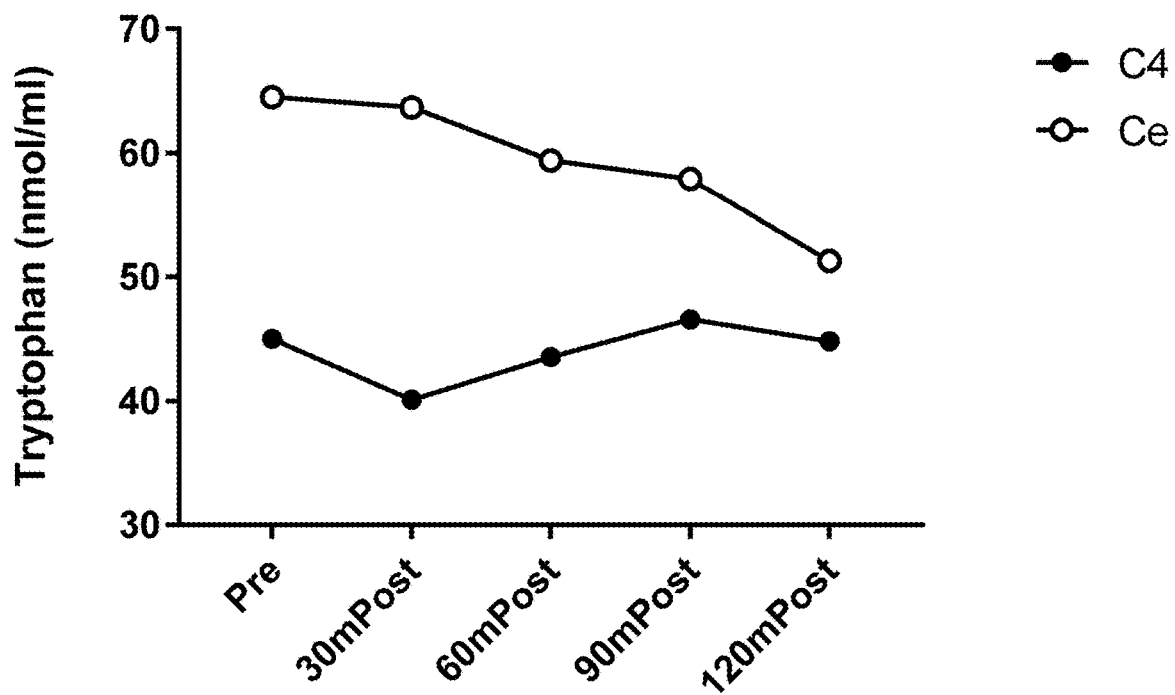
FIG. 8 shows plasma tryptophan concentrations following administration of disclosed compositions, according to certain embodiments.

Results: FIG. 8 shows plasma tryptophan concentrations after ingestion of C4 and CE conditions. Both conditions demonstrated decreases in plasma tryptophan concentration over the time course (−20.5% to −0.4%). At 90 mPost, Condition C4 marginally increased over Pre values (3.5%, 1.58 nmol/l).

Phenylalanine

TABLE 8

Plasma Phenylalanine Concentrations After Ingestion of C4 and CE Conditions (nmol/l).

|    | Pre   | 30 mPost      | 60 mPost      | 90 mPost       | 120 mPost      |
|----|-------|---------------|---------------|----------------|----------------|
| C4 | 48.61 | 42.44         | 40.84         | 46.94          | 45.40          |
| Ce | 59.22 | 62.78         | 61.24         | 53.24          | 57.33          |
|    |       | Percent and Delta Change Relative to Baseline Values | | | |
| C4 | 48.61 | −12.7%, −6.17 | −16.0%, −7.78 | −3.5%, −1.68   | −6.6%, −3.21   |
| Ce | 59.22 | 6.0%, 3.55    | 3.4%, 2.02    | −10.1%, −5.98  | −3.2%, −1.89   |

Figure 9:
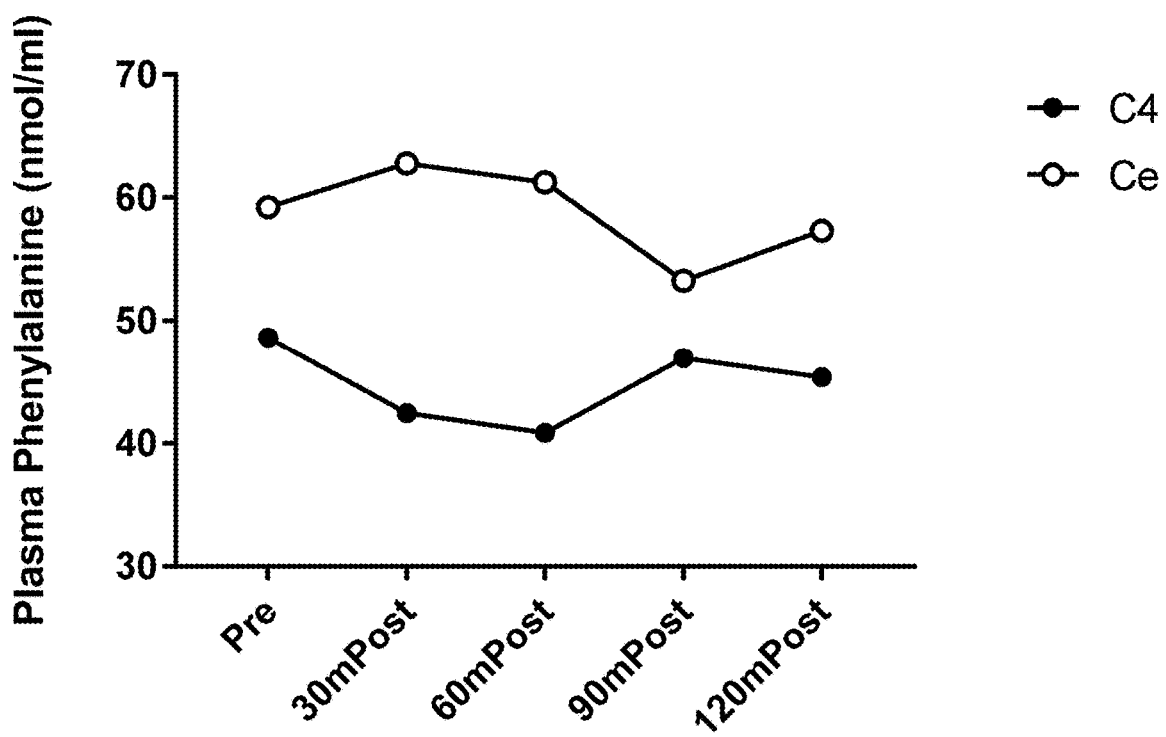
FIG. 9 shows plasma phenylalanine concentrations following administration of disclosed compositions, according to certain embodiments.

Results: FIG. 9 shows plasma phenylalanine concentrations after ingestion of C4 and CE conditions. Condition C4 demonstrated lower plasma phenylalanine concentrations at every investigated time point relative to Pre values (−16.0% to −3.5%). However, Condition Ce had higher levels at 30 and 60 mPost ingestion relative to Pre values (6.0% and 3.4%, respectively).

Lysine

TABLE 9

Plasma Lysine Concentrations After Ingestion of C4 and CE Conditions (nmol/l).

|    | Pre    | 30 mPost      | 60 mPost    | 90 mPost        | 120 mPost      |
|----|--------|---------------|-------------|-----------------|----------------|
| C4 | 121.19 | 135.48        | 128.45      | 134.15          | 171.18         |
| Ce | 134.69 | 174.66        | 176.01      | 109.39          | 160.37         |
|    |        | Percent and Delta Change Relative to Baseline Values | | | |
| C4 | 121.19 | 11.8%, 14.29  | 60%, 7.26   | 10.7%, 12.97    | 41.3%, 50.00   |
| Ce | 134.69 | 29.7%, 39.97  | 30.7%, 41.31| −18.8%, −25.31  | 19.1%, 25.68   |

Figure 10:
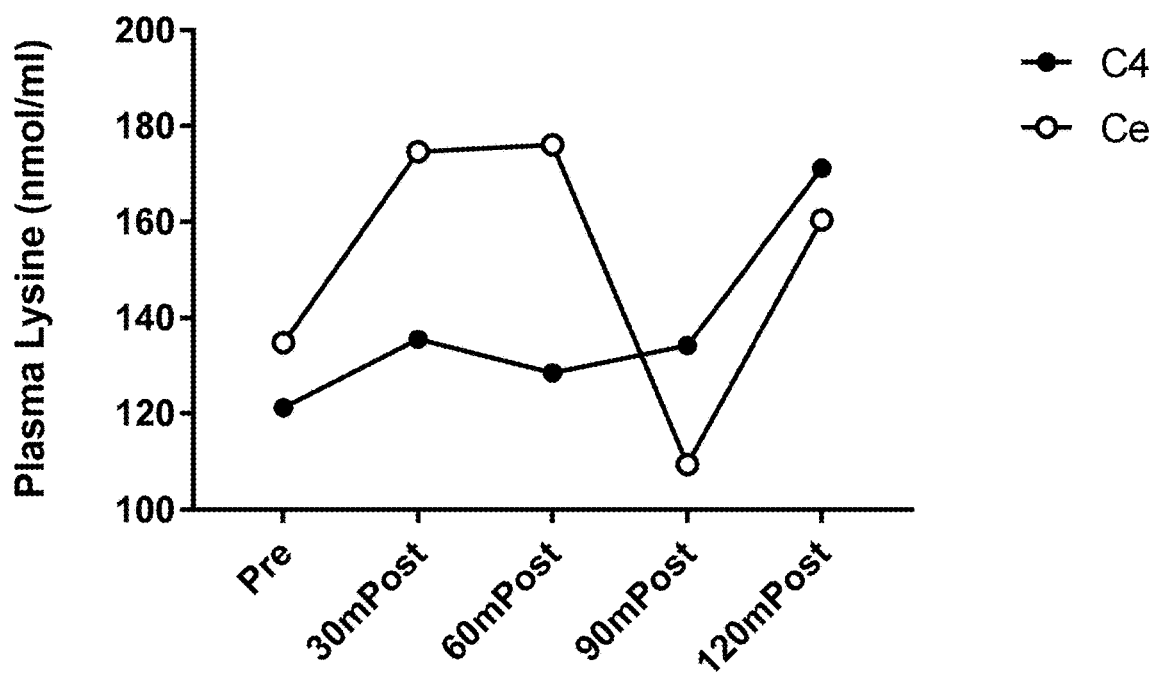
FIG. 10 shows plasma lysine concentrations following administration of disclosed compositions, according to certain embodiments.

Results: FIG. 10 shows plasma lysine concentrations after ingestion of C4 and CE conditions Both conditions demonstrated elevations in plasma lysine concentrations at 30, 60, and 120 mPost ingestion (6.0% to 41.3%). The increase observed at 30 mPost and 60 mPost was 2.8× and 5.7× greater in Condition Ce, respectively. The increase at 120 mPost ingestion was 19× greater in Condition C4 than Ce. Interestingly, Condition Ce experienced a drop of −18.8% in plasma lysine concentration relative to the Pre value.
Total FAA

TABLE 10

Total Plasma EAA Concentrations After Ingestion of C4 and CE Conditions (nmol/l)

|  | Pre | 30 mPost | 60 mPost | 90 mPost | 120 mPost |
|---|---|---|---|---|---|
| C4 | 689.38 | 754.23 | 685.20 | 785.26 | 801.61 |
| Ce | 987.21 | 1252.77 | 1058.54 | 872.56 | 927.87 |
|  |  | Percent and Delta Change Relative to Baseline Values |  |  |  |
| C4 | 689.38 | 9.4%, 64.86 | −0.6%, −4.18 | 13.9%, 95.88 | 16.3%, 112.23 |
| Ce | 987.21 | 26.9%, 265.57 | 7.2%, 71.33 | −11.6%, −114.65 | −6.0%, −59.34 |

Figure 11:
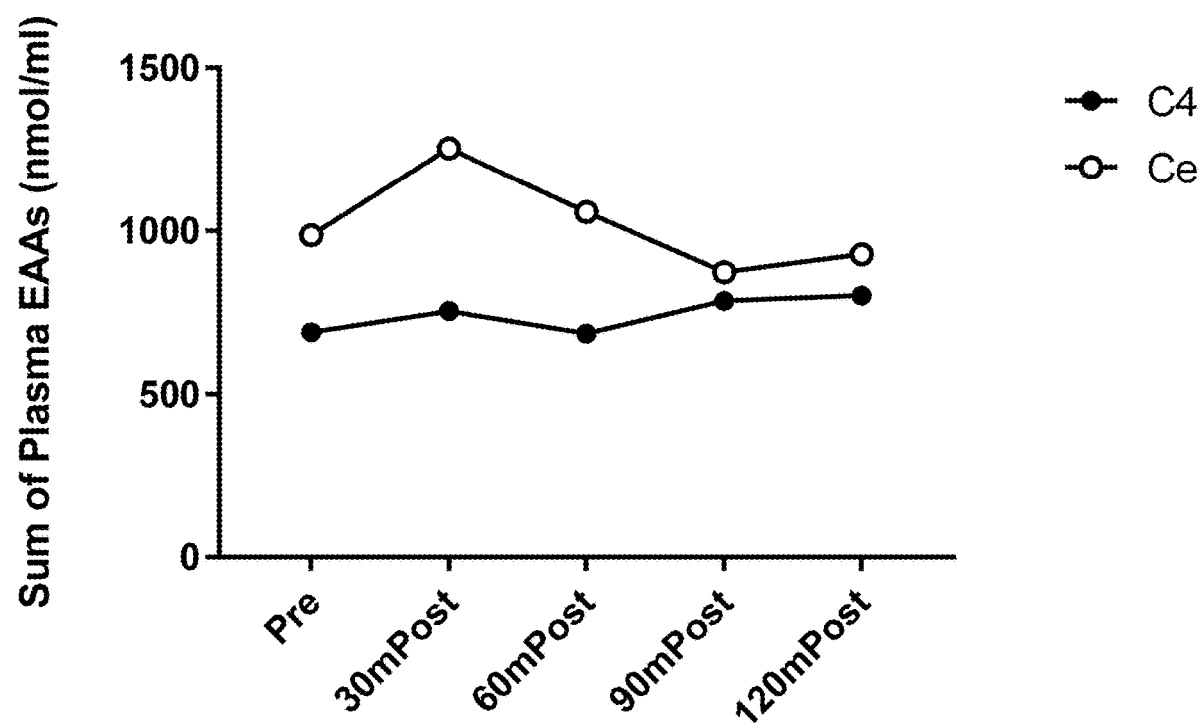
FIG. 11 shows total plasma essential amino acids (EAAs) following administration of disclosed compositions, according to certain embodiments.

Results: FIG. 11 shows total plasma EAA concentrations after ingestion of C4 and CE conditions. Condition C4 demonstrated increases in total EAA concentration at 30, 60, and 120 mPost ingestion (9.4% to 16.3%) relative to baseline; however, a very small decrease was noted at 60 mPost (−0.6%). Condition Ce demonstrated increases at 30 and 60 mPost (7.2% to 26.9%). The largest increase in total EAA concentration over the time trial occurred in Condition Ce at 30 mPost (26.9%, 265.57 nmol/l); this increase was 4× greater than Condition C4 at 30 mPost. Lastly, Condition Ce experienced decreases at 90 and 120 mPost (−11.6% and −6.0%, respectively).

Figure 12:
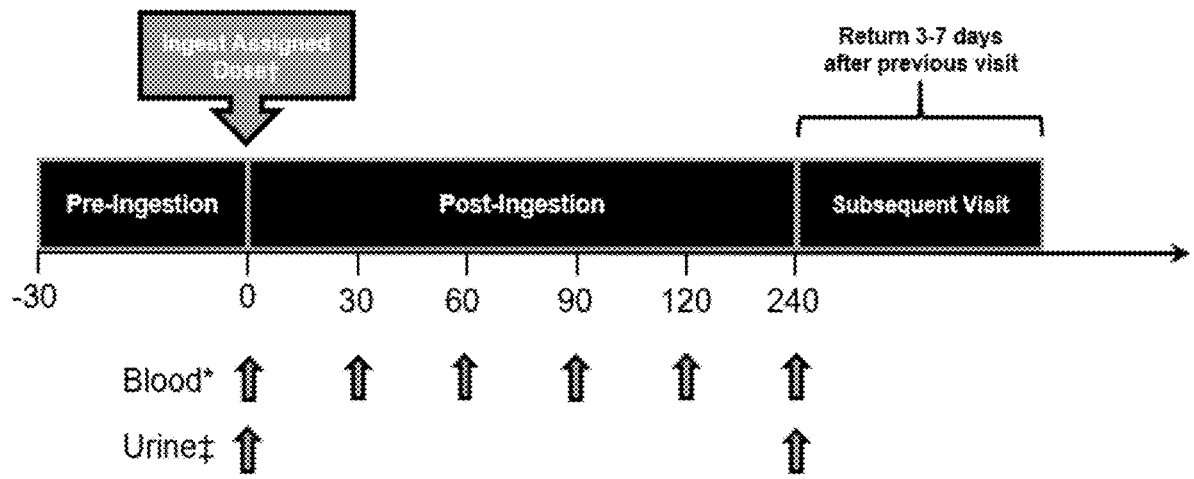
FIG. 12 shows a schematic representation of the experimental protocol for one example.

Another exemplary study was done on a male subject. The subject reported to the laboratory after an eight hour fast. Following and eight hour fast, the subject was given a standardized meal plan for two days prior to testing. The subject had his resting heart rate, blood pressure, body mass, height, and body measured using DEXA. Additionally, a urine sample was taken for baseline assessment of clinical safety, amino acid retention, and hydration status. A venous blood sample (10 mL) was be collected from a forearm vein prior to the subject being administrated, in a double-blind fashion a single dose of either leucine (2-gram dose), dileucine (2-gram dose) or leucine (1 grams)+dileucine (1 grams). Subsequent venous blood samples were to be collected 30, 60, 90, 120 and 240 minutes after ingestion of their assigned composition. After blood samples were taken the subject was given 250 mL of cold water to ingest. A second urine sample was taken at 240 minutes after ingestion of the composition. The methodology is shown schematically in FIG. 12.

All blood samples were processed to allow for determination of amino acid concentrations. The blood samples collected at 0 and 240-minutes were also processed for determination of a comprehensive metabolic panel and complete blood count (CBC) with platelet differentials. Both urine samples were processed to allow for determination of amino acid retention, clinical urinalysis, and basic safety parameters (e.g., creatinine). Upon processing, all blood and urine samples were stored at −80° C. The subject returned approximately 3-7 days after completion of the previous study visit to complete identical testing sessions as previously described while receiving the other treatments.

Plasma essential amino acids (threonine, methionine, lysine, histidine, valine, tryptophan, leucine, phenylalanine, isoleucine) were analyzed by LC/MS/MS and plasma dileucine was analyzed by GC/MS.

TABLE 11

Leucine-Leucine concentration: nmol/mL, Amino Acid concentration: μmol/L,
BLOD: Concentration of Leu-Leu in sample is below level of detection.

| LIMS No. | Leucine-Leucine | threonine | methionine | lysine | histidine | valine | tryptophan | leucine | phenylalanine | isoleucine |
|---|---|---|---|---|---|---|---|---|---|---|
| | | | | 2 g Dileucine | | | | | | |
| 8009985 | BLOD | 72.2 | 20.1 | 100.7 | 46.0 | 213.1 | 69.7 | 84.9 | 35.3 | 60.3 |
| 8009986 | BLOD | 74.2 | 17.7 | 96.5 | 46.9 | 212.3 | 56.7 | 100.5 | 30.4 | 59.5 |
| 8009987 | BLOD | 73.5 | 17.9 | 101.7 | 47.8 | 216.5 | 57.8 | 152.4 | 30.0 | 58.8 |
| 8009988 | 43.1 | 66.5 | 15.2 | 96.6 | 44.2 | 185.5 | 39.9 | 151.7 | 27.5 | 46.0 |
| 8009989 | <3.13 | 49.4 | 14.1 | 93.9 | 45.5 | 158.2 | 54.3 | 106.0 | 27.0 | 34.7 |
| | | | | 2 g Leucine | | | | | | |
| 8009990 | N/A | 56.8 | 16.7 | 89.7 | 42.4 | 198.1 | 56.1 | 83.1 | 29.2 | 59.8 |
| 8009991 | N/A | 67.2 | 19.2 | 100.6 | 46.1 | 214.6 | 61.9 | 159.3 | 31.8 | 64.9 |
| 8009992 | N/A | 64.1 | 16.6 | 95.0 | 42.5 | 201.7 | 45.0 | 279.6 | 50.2 | 59.4 |
| 8009993 | N/A | 64.2 | 15.1 | 96.4 | 42.2 | 180.6 | 55.7 | 166.2 | 23.9 | 43.2 |
| 8009994 | N/A | 65.0 | 13.9 | 95.2 | 42.3 | 165.4 | 76.5 | 138.9 | 23.0 | 38.7 |
| 8009995 | N/A | 52.6 | 12.5 | 91.6 | 40.4 | 153.7 | 50.3 | 110.6 | 22.4 | 35.6 |
| 8009996 | N/A | 52.4 | 14.0 | 89.6 | 42.8 | 152.5 | 46.3 | 93.1 | 25.1 | 39.0 |

TABLE 11-continued

Leucine-Leucine concentration: nmol/mL, Amino Acid concentration: µmol/L,
BLOD: Concentration of Leu-Leu in sample is below level of detection.

| LIMS No. | Leucine-Leucine | threonine | methionine | lysine | histidine | valine | tryptophan | leucine | phenylalanine | isoleucine |
|---|---|---|---|---|---|---|---|---|---|---|
| | | | | 1 g Dileucine + 1 g Leucine | | | | | | |
| 8009997 | <3.13 | 75.4 | 20.7 | 109.9 | 48.9 | 254.0 | 47.9 | 99.2 | 26.9 | 84.4 |
| 8009998 | BLOD | 84.0 | 23.5 | 107.7 | 47.7 | 245.8 | 56.0 | 94.9 | 31.3 | 78.8 |
| 8009999 | BLOD | 87.0 | 22.1 | 105.7 | 48.7 | 250.6 | 51.7 | 114.7 | 30.7 | 79.7 |
| 8010000 | BLOD | 78.2 | 19.4 | 102.0 | 45.2 | 224.4 | 45.5 | 173.2 | 27.4 | 69.9 |
| 8010001 | 62.4 | 80.4 | 18.5 | 108.3 | 45.3 | 216.3 | 44.9 | 183.2 | 26.2 | 61.5 |
| 8010002 | <3.13 | 75.2 | 17.0 | 102.2 | 44.3 | 196.9 | 46.6 | 143.9 | 23.0 | 50.4 |
| 8010003 | <3.13 | 57.8 | 14.5 | 100.1 | 45.1 | 178.8 | 49.2 | 106.3 | 25.0 | 44.1 |

Figure 13:
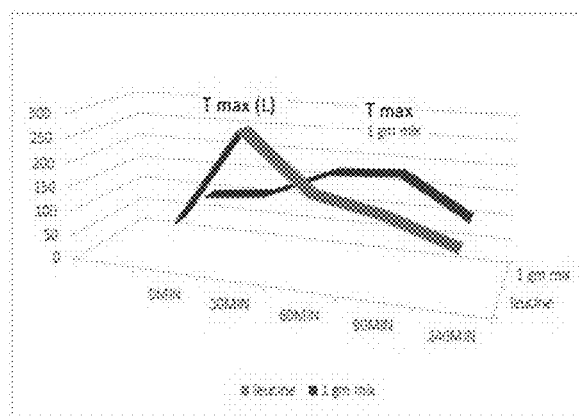
FIG. 13 shows leucine Tmax following administration of disclosed compositions, according to certain embodiments.
Figure 14:
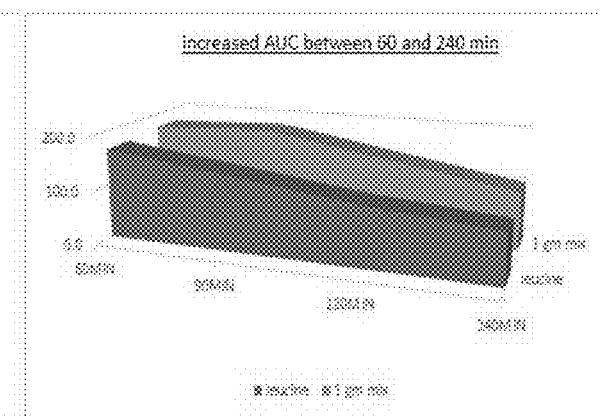
FIG. 14 shows leucine AUC following administration of disclosed compositions, according to certain embodiments.

Individual amino acid concentrations for all three treatments at various timepoints can be found in Table 11. The two treatments containing dileucine (2 g dileucine and 1 g leucine plus 1 g dileucine) resulted in measurable increases in plasma dileucine levels. In contrast to leucine (2 g) alone, the addition of dileucine (1 g) to leucine (1 g) delayed the time to reach maximum leucine concentrations. FIGS. 13 and 14 show a comparison of leucine Tmax and AUC after administration of leucine (2 g) or a mixture of leucine (1 g) and dileucine (1 g).

Another exemplary study was done to measure muscle protein synthesis. Two subjects came to the laboratory after a seven hour, overnight fast. A baseline blood sample was taken. Then a primed (2.0 µmol·kg−1), continuous infusion (0.05 µmol·kg−1·min−1) of L-[ring-13C6]-phenylalanine and L-[15N]-phenylalanine was started in one catheter.

Isotopes (from Cambridge Isotopes Inc., Andover, Mass.) were dissolved in 0.9% saline, filtered through a 0.2-µm filter, and infused using a calibrated syringe pump (from Harvard Apparatus, Holliston, Mass.). After obtaining steady-state enrichment, the L-[15N]-phenylalanine tracer infusion was stopped at t=0.

Figure 15:
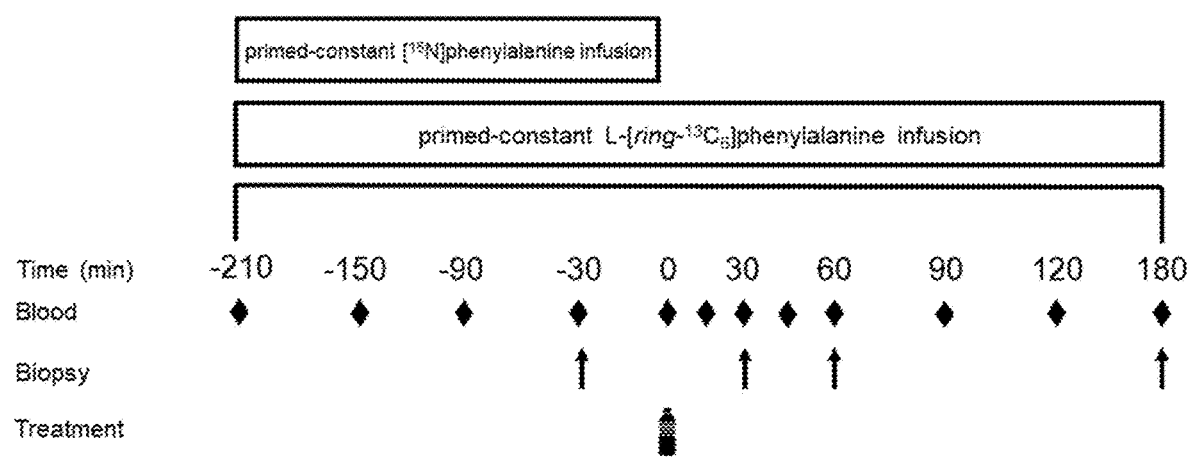
FIG. 15 shows a schematic representation of the experimental protocol for one example.

Repeated muscle biopsy sampling was done throughout the infusion trial for the determination of muscle protein synthesis (based on L-[ring-13C6]-phenylalanine incorporation) before and after the ingestion of 2 g leucine or 2 g dileucine. Biopsies (~100 mg wet weight) were obtained from the middle region of the vastus lateralis under anesthetic (Lidocaine HCl 1%) with a 5 mm Bergstrom needle custom-modified for manual suction. A schematic representation of the experimental protocol can be found in FIG. 15.

Figure 16:
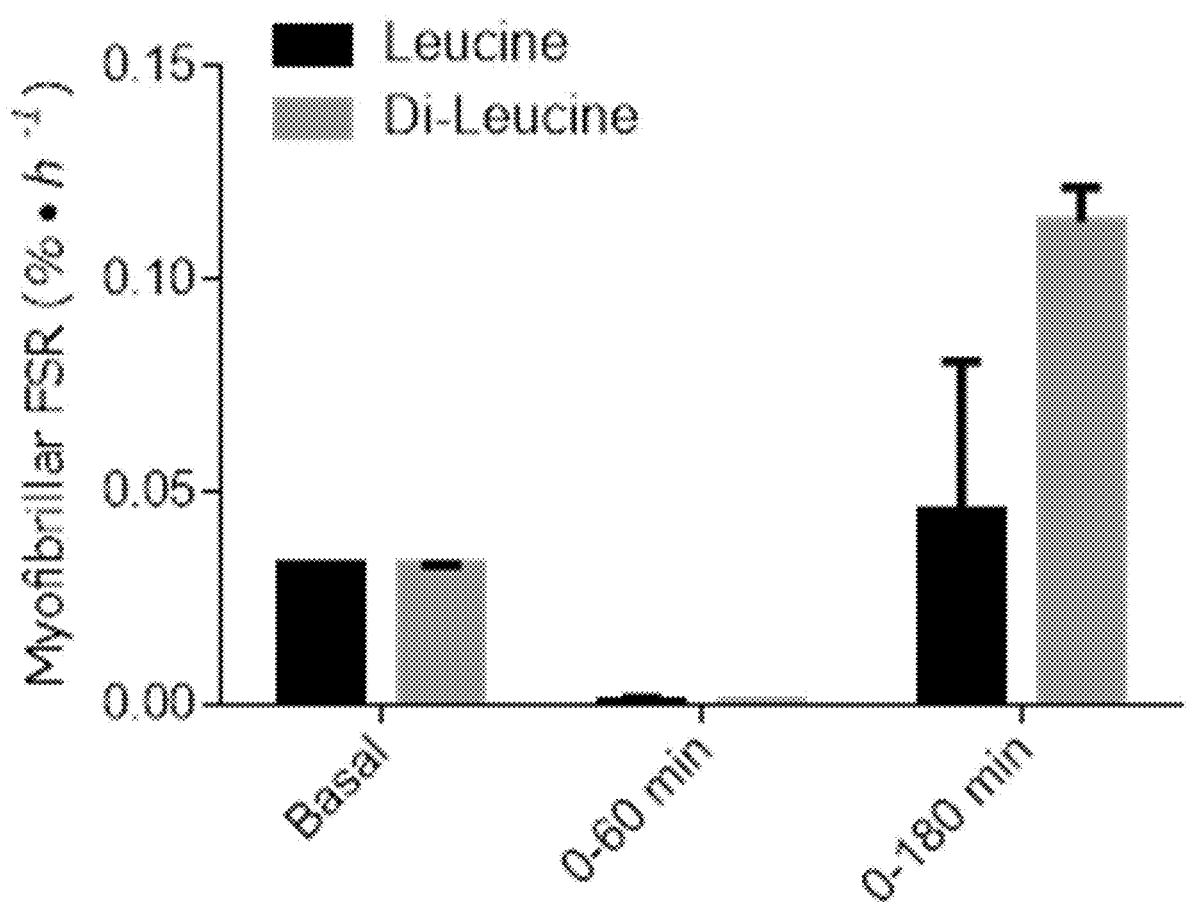
FIG. 16 shows exemplary plasma muscle protein synthesis data from muscle biopsy following administration of disclosed compositions, according to certain embodiments.

FIG. 16 shows muscle protein synthesis from muscle biopsies in subjects administered either leucine or di-leucine. Subjects receiving di-leucine showed significantly increased myofibrillar FSR 180 minutes post challenge that subjects receiving leucine.

Although the disclosure has been described with reference to preferred embodiments, persons skilled in the art will recognize that changes may be made in form and detail without departing from the spirit and scope of the disclosed apparatus, systems and methods.

What is claimed is:

1. A composition for increasing muscle protein synthesis comprising:
   a. dileucine, and
   b. leucine
   wherein the dileucine is present in an amount of at least about 50% (w/w) of the combined weight of dileucine and leucine.

2. The composition of claim 1, wherein the dileucine is present in amount of about 90% (w/w).

3. The composition of claim 2, wherein the dileucine is present in amount of about 80% (w/w).

4. The composition of claim 3, wherein the dileucine is present in amount of about 70% (w/w).

5. The composition of claim 4, wherein the dileucine is present in amount of about 60% (w/w).

6. The composition of claim 5, wherein the composition further comprises a pharmaceutical carrier.

7. A method for treating muscle atrophy in a subject or preventing muscle atrophy in a subject at risk for muscle atrophy, the method comprising administering to the subject an effective amount of a composition comprising leucine and dileucine wherein the dileucine is present in an amount of at least about 50% (w/w) of the combined weight of dileucine and leucine.

8. The method of claim 7, wherein the dileucine is present in amount of about 90% (w/w).

9. The method of claim 8, wherein the dileucine is present in amount of about 70% (w/w).

10. The method of claim 9, wherein the dileucine is present in amount of about 60% (w/w).

11. The method of claim 7, wherein the administration of the composition to the subject synergistically increases the plasma levels of leucine relative to administration of a composition comprising leucine without dileucine.

12. The method of claim 7, wherein the subject has sarcopenia.

13. The method of claim 12, wherein in the composition is administered in a therapeutically effective amount.

14. A method for increasing muscle protein synthesis in a subject, the method comprising administering to the subject an effective amount of a composition comprising leucine and di-leucine, wherein the dileucine is present in an amount of at least about 50% (w/w) of the combined weight of dileucine and leucine and wherein administration of the composition of to the subject increases muscle protein synthesis in the subject.

15. The method of claim 14, wherein the composition further comprises at least one peptide chosen from: tri-leucine, and Leu-Leu-R, wherein R is an amino acid or an amino acid derivative, and pharmaceutically acceptable salts thereof.

16. The method of claim 15, wherein the dileucine is present in amount of about 90% (w/w).

17. The method of claim 16, wherein the dileucine is present in amount of about 70% (w/w).

18. The method of claim 17, wherein the amount of the composition administered is at least about 200 mg.

19. The method of claim 15, wherein the administration of the composition to the subject synergistically increases the plasma levels of leucine relative to administration of a composition comprising leucine without dileucine.

20. The method of claim 15, wherein the administration of the composition to the subject synergistically increases muscle mass and/or muscular strength relative to administration of a composition comprising leucine without dileucine.

* * * * *